US011738157B2

(12) United States Patent
Chowdhury

(10) Patent No.: US 11,738,157 B2
(45) Date of Patent: Aug. 29, 2023

(54) INJECTION DEVICE

(71) Applicant: NDM TECHNOLOGIES LIMITED, Loughborough (GB)

(72) Inventor: Dewan Fazlul Hoque Chowdhury, Leicestershire (GB)

(73) Assignee: NDM TECHNOLOGIES LIMITED, Loughborough (GB)

( * ) Notice: Subject to any disclaimer, the term of this patent is extended or adjusted under 35 U.S.C. 154(b) by 117 days.

(21) Appl. No.: 16/759,274

(22) PCT Filed: Oct. 26, 2018

(86) PCT No.: PCT/GB2018/053108
§ 371 (c)(1),
(2) Date: Apr. 24, 2020

(87) PCT Pub. No.: WO2019/081947
PCT Pub. Date: May 2, 2019

(65) Prior Publication Data
US 2021/0178085 A1 Jun. 17, 2021

(30) Foreign Application Priority Data
Oct. 26, 2017 (GB) ...................................... 1717647

(51) Int. Cl.
*A61M 5/42* (2006.01)
*A61M 5/24* (2006.01)
(Continued)

(52) U.S. Cl.
CPC .............. *A61M 5/425* (2013.01); *A61M 5/24* (2013.01); *A61M 5/329* (2013.01);
(Continued)

(58) Field of Classification Search
CPC ...... A61M 5/425; A61M 5/24; A61M 5/3287; A61M 5/329; A61M 5/3298; A61M 5/45;
(Continued)

(56) References Cited

U.S. PATENT DOCUMENTS

2002/0123740 A1 9/2002 Flaherty et al.
2008/0015624 A1* 1/2008 Sonoda .................. A61M 5/425
606/185
(Continued)

FOREIGN PATENT DOCUMENTS

CN 1612758 5/2005
CN 204274550 U 4/2015
(Continued)

OTHER PUBLICATIONS

International Search Report and Written Opinion, PCT/GB2018/053108, NDM Technologies Limited (dated Jan. 17, 2019).
(Continued)

*Primary Examiner* — Kami A Bosworth
*Assistant Examiner* — Antarius S Daniel
(74) *Attorney, Agent, or Firm* — Foley & Lardner LLP

(57) ABSTRACT

The invention relates to a needle delivery device comprising a device body; one or more skin pinching members attached to the device body, the skin pinching members being moveable to pinch a longitudinal fold of skin of a patient. The device also comprises a drive mechanism configured to drive a needle out of the device body and along a needle path into the longitudinal fold of skin pinched between the pinching members, and subsequently withdraw the needle, the needle path extending substantially parallel to the surface of the patient.

18 Claims, 12 Drawing Sheets

(51) Int. Cl.
*A61M 5/32* (2006.01)
*A61M 5/46* (2006.01)

(52) U.S. Cl.
CPC ........ *A61M 5/3287* (2013.01); *A61M 5/3298* (2013.01); *A61M 5/46* (2013.01); *A61M 2205/13* (2013.01); *A61M 2205/3331* (2013.01)

(58) Field of Classification Search
CPC .. A61M 5/42; A61M 5/4248; A61M 2205/13; A61M 2205/3331
See application file for complete search history.

(56) References Cited

U.S. PATENT DOCUMENTS

| | | |
|---|---|---|
| 2009/0082730 A1 | 3/2009 | Nguyen et al. |
| 2010/0010374 A1 | 1/2010 | Escutia et al. |
| 2011/0303734 A1 | 12/2011 | Whitman |
| 2014/0107697 A1 | 4/2014 | Patani et al. |
| 2014/0128815 A1 | 5/2014 | Cabiri et al. |
| 2014/0288386 A1* | 9/2014 | Zand .................. A61B 5/0059 600/301 |
| 2015/0173996 A1* | 6/2015 | Grez ................... A61B 5/0057 600/587 |
| 2015/0209508 A1 | 7/2015 | Constantineau et al. |
| 2016/0144137 A1* | 5/2016 | Shapiro .................. A61M 5/46 604/506 |
| 2016/0331910 A1 | 11/2016 | Imai et al. |
| 2018/0133395 A1* | 5/2018 | Margairaz ........... A61M 5/2033 |
| 2019/0022306 A1* | 1/2019 | Gibson ................. A61M 5/142 |
| 2019/0133734 A1* | 5/2019 | Erickson ................. A61M 5/46 |
| 2019/0336679 A1* | 11/2019 | Staub .................... A61M 5/158 |

FOREIGN PATENT DOCUMENTS

| | | |
|---|---|---|
| CN | 105979987 | 9/2016 |
| EP | 3 100 756 | 12/2016 |
| FR | 757501 A | 12/1933 |
| JP | 2013-085596 | 5/2013 |
| JP | 2015-144636 | 8/2015 |
| WO | WO-1994/08526 | 4/1994 |
| WO | WO-00/23132 A1 | 4/2000 |
| WO | WO-2003/090630 | 11/2003 |
| WO | WO-2008/005385 | 1/2008 |
| WO | WO-2015/168300 A1 | 11/2015 |

OTHER PUBLICATIONS

CN Search Report on CN Application No. 2018800762251 dated Aug. 30, 2021.

* cited by examiner they claim the

INJECTION DEVICE

CROSS-REFERENCE TO RELATED APPLICATIONS

This application is a National Stage Application of PCT/GB2018/053108, filed Oct. 26, 2018, which claims the benefit of and priority to Great Britain Patent Application No. 1717647.0, filed Oct. 26, 2017, the entire contents of which are incorporated herein by reference.

This invention relates to an injection device.

It is known to deliver drugs through the skin, i.e. transdermally, by using a needle in conjunction with a delivery device.

These devices can be complex, cumbersome and expensive.

Many drugs, in particular biologics have low potency or generally require large volumes to be administered by injection. Delivery of large volumes of drugs by injection often requires body-worn devices to enable the drug to be injected over an extended period of time. Concentrating the drug to reduce the volume and making it more viscous poses challenges such as irritation, and the need for substantial injection forces. Body worn devices allow large volumes to be injected over periods ranging from 10's of minutes to several hours. However, bolus doses are required to be administered as rapidly as possible, to ensure the correct plasma drug concentrations can be reached, hence it is preferable to deliver bolus doses very rapidly.

It is preferable therefore to have a device that can inject a large volume of drug as a bolus, very rapidly, within a few minutes. This invention describes means of achieving this.

According to the present invention, there is provided a needle delivery device comprising: a device body;

one or more skin pinching members attached to the device body, the skin pinching members being moveable to pinch a longitudinal fold of skin of a patient; and a drive mechanism configured to drive a needle out of the device body and along a needle path into the longitudinal fold of skin pinched between the pinching members, and subsequently withdraw the needle, the needle path extending substantially parallel to the surface of the patient.

The needle device preferably comprises a pharmaceutical composition delivery mechanism configured to deliver a pharmaceutical composition through the needle.

Optionally, the needle path within the device body changes direction as it leaves the device body.

Preferably, the needle delivery device comprises at least one needle. The device can also comprise multiple needles. Advantageously, at least a portion of the at least one needle can be flexible.

The needle delivery device can also further comprise a guide member configured to guide the at least one needle along the needle path. In accordance with one aspect, the guide member is, or includes, a roller.

Preferably, the at least one needle is configured to revert to an elongated straight shape after passing through an arcing pathway.

In accordance with one aspect of the invention, when positioned within the device body the at least one needle is covered by a protective sheath. The protective sheath has a rigid section and a flexible section, wherein the rigid section surrounds the tip of the at least one needle and comprises an opening to allow the at least one needle to exit the rigid section on actuation of the drive mechanism.

Optionally, the protective sheath comprises a sealing membrane covering the opening, wherein the sealing membrane is penetrable by the at least one needle.

In accordance with the present invention, the at least one needle has a length of greater than about 12 mm, preferably from about 20 mm to about 200 mm, more preferably from about 20 mm to about 100 mm, more preferably from about 20 mm to about 50 mm.

Preferably, the needle delivery device comprises a pharmaceutical composition reservoir in fluid communication with the pharmaceutical composition delivery mechanism.

Advantageously, the needle delivery device can further comprise a sensor mechanism to sense the pinching of the longitudinal fold of skin.

In accordance with one embodiment there is provided a method of administering a pharmaceutical composition to a patient comprising using a needle delivery device of any preceding claim. Preferably, the pharmaceutical composition is delivered as the at least one needle is being retracted through the pinched skin.

In a further aspect of the present invention there is provided a device for pinching the skin comprising:

a device body;

one or more skin pinching members attached to the device body, the skin pinching members being moveable to pinch a longitudinal fold of skin of a patient; and sensing means to sense the pinching of the longitudinal fold of skin.

Preferably the device further comprises:

a drive mechanism configured to, in use, drive a needle out of the device body and along a needle path into the longitudinal fold of skin pinched between the pinching members, the needle path extending substantially parallel to the surface of the patient; and a pharmaceutical composition delivery mechanism configured to deliver a pharmaceutical composition through the needle.

Advantageously, the sensing means comprises at least one light source and at least one light sensor to detect the presence of pinched skin therebetween.

Alternatively, or in addition to the light sensor, the sensing means comprises at least one mechanical switch to detect contact with pinched skin.

The sensing means can comprise an electrical sensor to detect contact with pinched skin.

Preferably, the sensing means is a pressure sensor.

The sensing means can comprise a plurality of sensing means to detect pinching along the length of the longitudinal fold of pinched skin.

In one aspect of the invention, the skin pinching member(s) are configured to automatically adjust based on the volume of the pharmaceutical composition injected into the skin; or wherein the skin pinching member(s) are configured to automatically adjust using pressure sensors based on the pressure of the pinched skin.

In accordance with one aspect of the invention there is provided a method of sensing the pinching of a longitudinal fold of skin comprising;

placing a device as described above in contact with the skin of a patient;

moving at least one skin pinching member to pinch a longitudinal fold of skin; sensing the pinching of the longitudinal fold of skin.

The method can further comprise the steps of:

driving at least one needle out of the device body and along a needle path into the longitudinal fold of skin pinched between the pinching members, the needle path extending substantially parallel to the surface of the patient; and delivering a pharmaceutical composition to the patient through the at least one needle as the needle is being withdrawn through the longitudinal fold of skin.

The present invention will now be described with reference to the figures, in which FIG. 1A is a plan view of a needle delivery device.

Figure 1A:
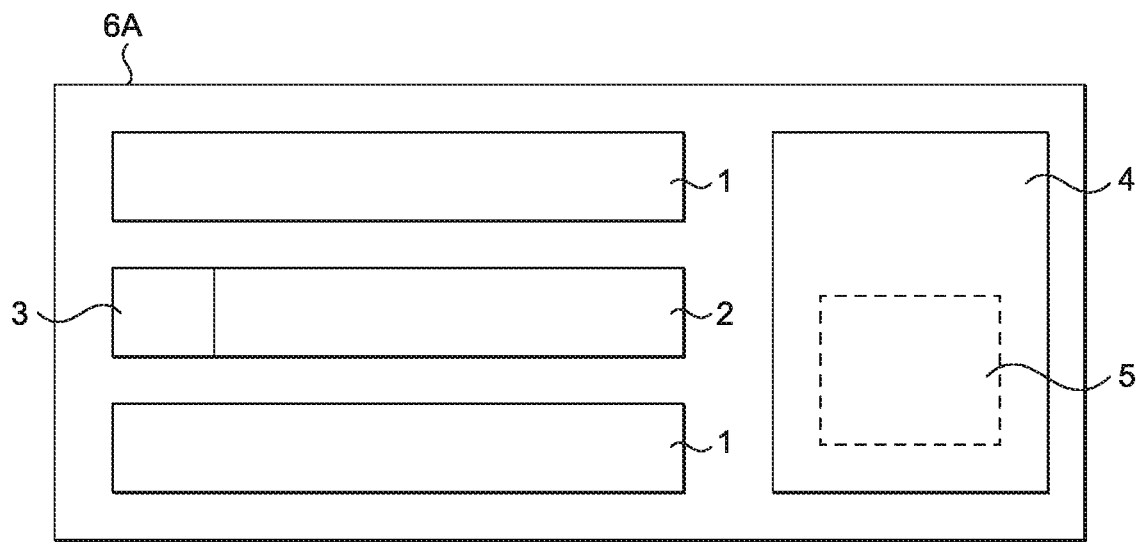
FIG. 1B is a plan view of another needle delivery device.

A device and method are described for injecting large volumes of drugs rapidly in a controlled manner, to either negate the need for a body-worn device or to minimise the duration of wear time required of a body worn device. The device pinches a longitudinal portion of the skin, creating a skin volume within which a needle can be inserted. The needle can then be gradually drawn away from the skin, whilst depositing continuous or intermittent drug volumes as the needle is drawn out of the skin, enabling a large volume to be distributed using single or multiple needles to within a precise depth within the skin, rapidly.

This invention relates to a device and method for rapidly injecting drug into the skin, in particular the invention relates to injecting drug formulations within the dermis or subcutaneous layer, or layers that do not reach the intramuscular tissue. Injecting a large volume requires the drug volume to disperse within the tissue, and this can only occur at a certain maximum rate, based on the local tissue circulation and intracellular uptake. Very rapid injection forces will lead to collateral damage of tissue, and bruising and inflammatory reactions hence it is preferable not to inject with very high forces to increase the delivery time.

Often the skin is pinched manually by the user to raise the tissue and allow the needle to be inserted.

This invention describes a method for pinching the skin over a longitudinal distance such that a significantly larger volume is available for the insertion of a significantly longer needle. It is intended that the needle would first penetrate the longitudinally-pinched region of the skin to a maximum distal position. The drug formulation would then be injected either at a constant force or intermittently as the needle is withdrawn, thus allowing a large volume of the drug to be injected over a larger skin volume at a rapid speed.

Normally 1 ml of drug can be injected into subcutaneous tissue within a period of 10-15 seconds. A volume of up to 20 ml would therefore require several minutes for administration, often over 30 minutes, since when a needle is inserted and a volume of for example 1 ml is injected, the local tissue is only able to take up 1 ml of the drug volume, and any further volume uptake in that specific region will lead to back flow, blockages in the needle, back pressure build-up, and tearing of intracellular tissue leading to tissue damage and bruising. It is not possible therefore to inject 10 ml in for example 100 to 150 seconds and the rate of injection flow may have to be reduced to less than 0.5 ml per minute to ensure the entire volume can be adequately taken up by the tissue.

However, the present invention allows the needle to be gradually retracted into new tissue space, allowing the faster delivery of a large volume of material to a patient. Therefore, as an example of using the invention, if 1 ml takes 10 seconds to inject, then 10 ml will take 100 seconds to inject.

This requires a needle that has sufficient rigidity to be inserted at longer depths of up to several centimeters. For example, an average subcutaneous injection needle is between 4 mm and 12 mm. However, in the present invention the needle may be as long as 100 cm or possibly longer depending where the device is applied. Such needle lengths have not been used for subcutaneous injections as standard practice.

In order to allow the needle to be inserted in the correct layer of tissue, e.g., fat layer, dermis, or subcutaneous layer, the needle must therefore be inserted into the skin horizontally and not vertically or at an angle to the skin. This is achieved by pinching the skin along a length that is greater than the intended distance of insertion of the needle, sufficiently that when the drug is injected it is retained within the skin. The needle is injected substantially parallel to the surface of the skin, after the skin is pinched to a height and length adequate for needle insertion, and the needle height relative to the pinched tissue may be adjusted to provide skin penetration to the desired tissue depth.

The pinching action may achieve one of a number of objectives:

Hold the skin in a loose pinched position to enable the drug volume to be injected along the length of the skin as the needle is retracted.

Pinch the skin tightly creating a longitudinal compressed region of the skin where there is a temporary hiatus in the blood supply and compression on nerve endings thus minimising the sensation of pain. This higher degree of constriction may be released once the needle has been inserted to the full distance, to enable a large volume of drug to be inserted without constricting the flow of the drug volume into the tissue.

An important feature of the pinching action is to ensure the skin is uniformly pinched along the entire length to avoid potential problems. For example, if a needle is inserted into tissue that is not uniformly pinched, the needle could exit the skin and re-enter further along, potentially causing injury as well as leading to loss of drug volume to the exterior of the skin. Indeed, in the event of normal (prior art) pinching of the skin for a subcutaneous injection, if the needle was inserted horizontally along the plane of the skin/body, the needle would protrude from the other side of the pinched tissue.

The uniformity of the skin pinching can be achieved using a number of methods:
- A mechanical barrier is positioned, in the form of a longitudinal groove within which the skin is pinched, such that the pinched skin takes the shape and volume of the groove/hollow chamber formed within the mechanical barrier.
- An optical detection method is used, for example using an LED and a diode to transmit light and detect the transmitted light, respectively. The skin pinching will only be deemed to have been successfully uniformly undertaken when light cannot be detected by the diode across the designated length of pinched tissue, when the skin is adequately and uniformly pinched. In the event light still passes to the detector the pinching action will occur again until no light passes through, as will be described below with reference to the figures.
- A series of mechanical switches positioned at the roof of the hollow chamber/groove, whereby each and every switch must be mechanically activated to confirm that the skin has been adequately pinched uniformly across the entire cross section.

In a further embodiment of the invention, in particular for very large volumes being injected, the pinching member(s) may be relaxed across the entire length of the skin, or towards the distal region of the skin/tip end of the needle, either in a single step or gradually, as the drug volume is being injected, in order to accommodate the increase in volume of the skin. The relaxing of the skin pinching member(s) may be pre-determined and automatically adjusted based on the volume injected for a given length, based on pre-determined increased in the skin volume, or it may be determined using pressure sensors against the roof and/or inner walls of the pinching member(s), whereby as the pressure exceeds a pre-determined value the pinching member is adjusted/relaxed to maintain the pressure at a given predetermined maximum value.

Turning to FIG. 1, a needle delivery device is shown having a device body 6. A pair of skin pinching members 1 are shown on the underside of the device, comprising two elongate bars that are generally parallel to each other.

In use, the device is placed in contact with the skin of a patient and the pair of skin pinching members 1 are moved towards each other. In doing so, they pinch a longitudinal fold of skin between them, along the length of the skin pinching members. The terms skin, or a fold of skin, are used here to refer to the outer tissue of the patient's body. So, a fold of skin also encompasses a fold of skin and some underlying tissue such as subcutaneous fat.

In the embodiment shown in FIG. 1, the device comprises two skin pinching members 1 which are both attached to the device body and are both moveable towards each other. In other embodiments, the device may comprise a first fixed pinching member and a second moveable pinching member which is moveable towards the first pinching member. This may include embodiments where the fixed pinching member is formed by part of the device body 6, which remains fixed and the other member moves to pinch the skin against the fixed side.

The device includes a pharmaceutical composition reservoir 2, pharmaceutical composition reservoir exit port 3, which may be a luer slip or luer lock or other connection means, via which the pharmaceutical composition is forced out of the reservoir 2. The plunger (in the case of the pharmaceutical composition reservoir being a pre-filled cartridge or syringe) is not shown here, neither is any other mode of forcing the drug out of the reservoir, and these such mechanisms are generally well understood in the state of the art. A needle hub and associated needle drive mechanism 5, are indicated together with an electronic control board 4 where the device is intended to be electro-mechanical rather than purely mechanical.

As mentioned above, in use the device forms a longitudinal fold of skin between the skin pinching members 1. The needle drive mechanism then drives the needle out of the device body 6 and into the formed fold of skin. As the needle passes out of the device body 6 and into the fold of skin it travels along a needle path that is substantially parallel to the surface of the patient. This allows the needle to penetrate through the fold of skin to a predetermined distance, whilst being kept to a controlled depth within the fold of skin.

The pharmaceutical composition delivery mechanism then delivers the pharmaceutical composition from the reservoir through the needle and into the patient. As mentioned above, delivering the composition as the needle is being withdrawn through the length of the fold of skin is advantageous as it allows for the rapid delivery of a large volume of material. The pharmaceutical composition can be delivered to the patient using a variety of methods, such as via a plunger mechanism that forces the contents of the reservoir (e.g. a vial or pre-filled syringe) through the bore of the needle. Where alternative collapsible reservoirs are used, containing a fluid communication connection with a suitably mounted needle, the contents of the reservoir may be dispensed by compressing the reservoir leading it to collapse as the content is expelled.

Figure 1B:
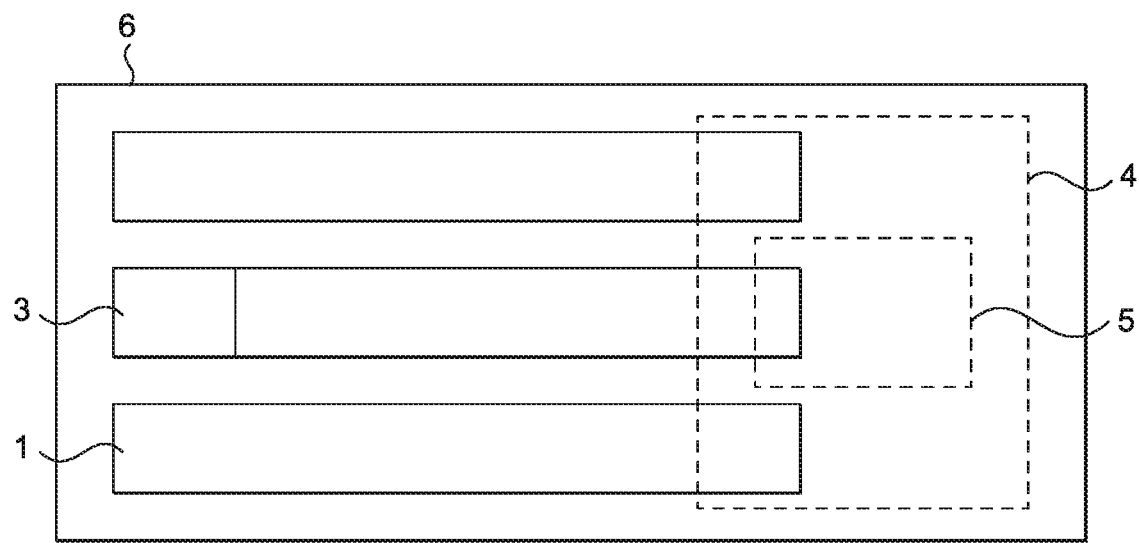

FIG. 1B shows a plan view of another embodiment of the device, with a needle hub overlapping the skin pinch members 1. So, unlike the device shown in FIG. 1A, this device has the needle drive mechanism located above the skin pinching members 1, rather than being located to one side of the skin pinching members 1.

The overlapping of the skin pinch member 1 by the needle hub 5 ensures that the skin is adequately compressed against the hub and unable to be displaced by any significant amount, allowing the needle to adequately penetrate the skin at the desired depth.

Figure 2:
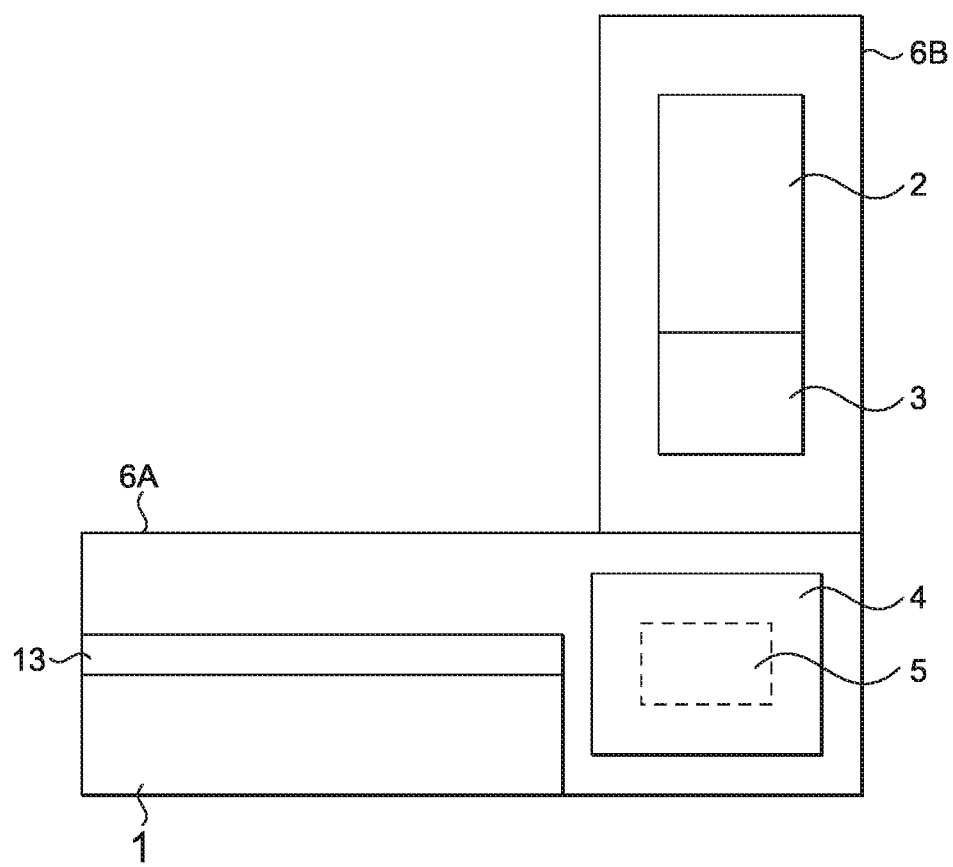
FIG. 2 is a cross section schematic of a needle delivery device showing a drug reservoir longitudinal to the needle.

FIG. 2 shows a cross-sectional side view of the device showing the needle drive mechanism 5 to one side of the skin pinching members 1. The drug reservoir 2 is located directly above the needle drive mechanism 5. and generally perpendicular to the skin pinching member 1. An upper region 13 is indicated within body 6 of the device, in the vicinity of the pinching members 1. The region 13 is provided with sensing means to confirm the uniformity of the skin pinch across the length of the skin pinching member, prior to insertion of the needle into the skin. The sensing means may comprise optical, mechanical and/or electrical sensors located in the region 13. It is advantageous to be able to sense or determine the uniformity of the longitudinal fold of skin.

Figure 3A:
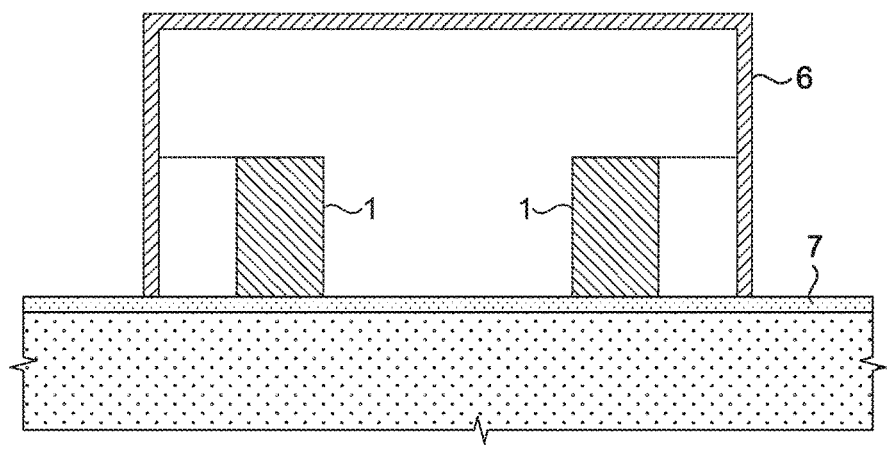
FIG. 3A is a front cross section of the device before activation.

FIG. 3A is a front cross section of the device showing the skin pinching members 1 end on within the body 6 of the device. The location of the pinching members 1 is shown relative to the device housing 6, and skin 7. This is the situation as the device is placed on the skin 7 of the patient but before the skin pinching members are moved towards each other.

Figure 3B:
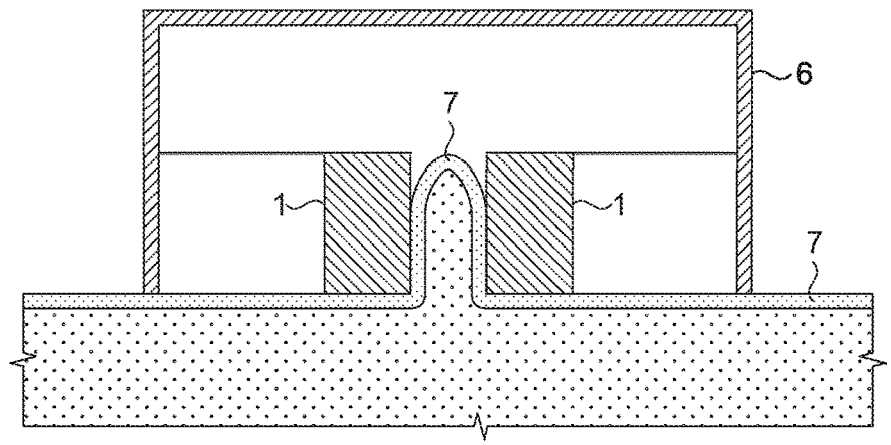
FIG. 3B is a front cross section of the device after activation.

FIG. 3B shows a front cross section of the device after the skin pinching members have been activated. The skin pinching members 1 have moved inwards to pinch the skin 7 within the groove/chamber between the skin pinching members 1 beneath the body 6 of the device, showing the cross section of a raised area of skin, which will be uniform across the length of the skin pinching member. In this embodiment, the outer casing 6 is shown to be stationary relative to the skin pinch members 1, whereby the latter expands inwards or is moved inwards to pinch the skin.

Figure 3C:
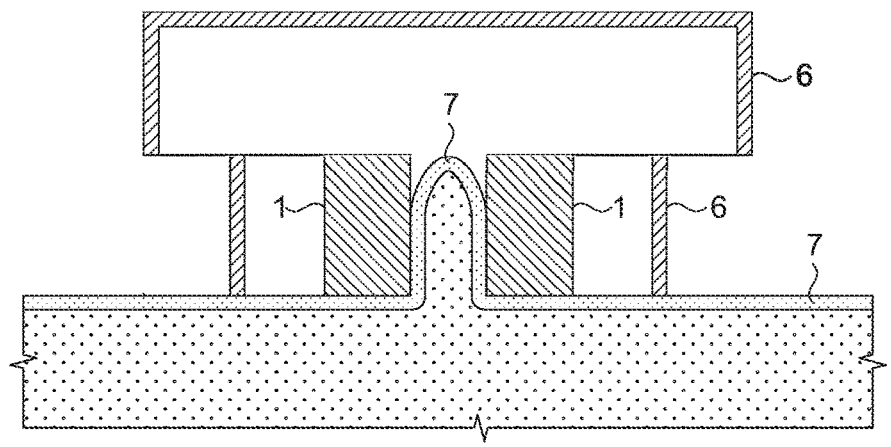
FIG. 3C is a front cross section of another device after activation.

FIG. 3C is a front cross-sectional view of the device showing the skin pinching members and the wall of the device body 6 moving in tandem. The embodiment shown in this figure differs from that shown in FIG. 3B as the outer casing also moves in with the skin pinch member 1, which may be preferable as a visual confirmation for the user that the skin pinch is complete.

Figure 4A:
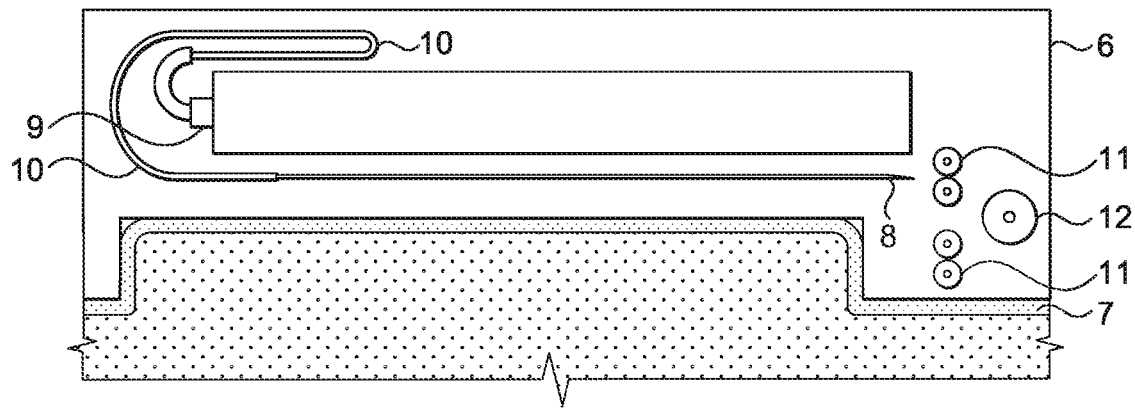
FIG. 4A is a side cross section of a device with a flexible needle.

FIG. 4A shows a longitudinal cross section schematic showing the skin 7 in a raised pinched state, within the chamber between the skin pinch members 1. A needle connection port 9 is shown connected to a flexi-rigid needle, whereby the flexi section 10 of the needle is connected directly to a rigid section 8, shown in a stationary position. The rigid section 8 of the needle can pass through compressing guide rollers 11 and single large guide roller 12 to force the needle to follow an arcing pathway. The flexi portion 9 of the needle may be produced from a thin walled flexible metal, or polymer such as polyvinyl acetate, polypropylene, or one of many other polymers known in the state of the art. The rigid section 8 may be produced from a plastic polymer too, though it is preferably produced from a metal such as stainless steel, or a shape memory metal such as nickel titanium, whereby the metal is rigid in that it maintains its elongated straight shape, but is able to pass through rollers through an arching pathway before reverting to a straight rigid position. The use of needles that comprise a flexible portion enables the device to be compact. The needle is directed through an opening in the body 6 of the device and then out towards the fold of skin.

Flexible needles can be produced to allow a 90 degree bend radius without fracturing or permanently deforming the needle. Such needles may be formed using metal alloys such as nickel titanium, stainless steel metals of very high aspect ratio, other inert metals, polymers such as nylon and polyester and medical grade polymers widely used in the construction of syringes. Flexible needles made from these materials would normally be produced through an extrusion mechanism. A combination of a metal tip and plastic body/conduit may also be used to form a flexible needle, wherein the metal tip provides a sharp mechanically strong leading tip. Flexible needles may be as small as 10's of microns thin, such as hollow fiber optic cables, through to standard 18 gauge at the tip, with equivalent or different diameter flexible conduit connected to the reservoir via a luer slip or luer lock connection, via which the drug may flow from the reservoir.

The needles used can be flexible along a portion or along all of its length. The needle may be formed from using metal alloys such as nickel titanium, stainless steel metals of very high aspect ratio, other inert metals, polymers such as nylon and polyester and medical grade polymers widely used in the construction of syringes. The needle can be formed through an extrusion process.

The needle 120 may instead have a flexible portion (e.g. a plastic body/conduit) and a rigid metal tip, such as that described hereinabove with reference to the first needle delivery device 10.

The drive mechanism may be mechanically operated using a series of rollers, pulleys and suitably mounted springs, or it may be electromechanically driven using actuators such as a combination of motors and gears, or linear actuators such as those constructed from shape memory metals.

The pharmaceutical composition reservoir is in fluid communication with an end of the needle. This may be a direct fluid communication or an indirect fluid communication via an intermediate member which permits such fluid communication. For example, there may be a flexible conduit connected at one end of the reservoir via a luer slip or luer lock connection, and at the other end to the needle.

Figure 4B:
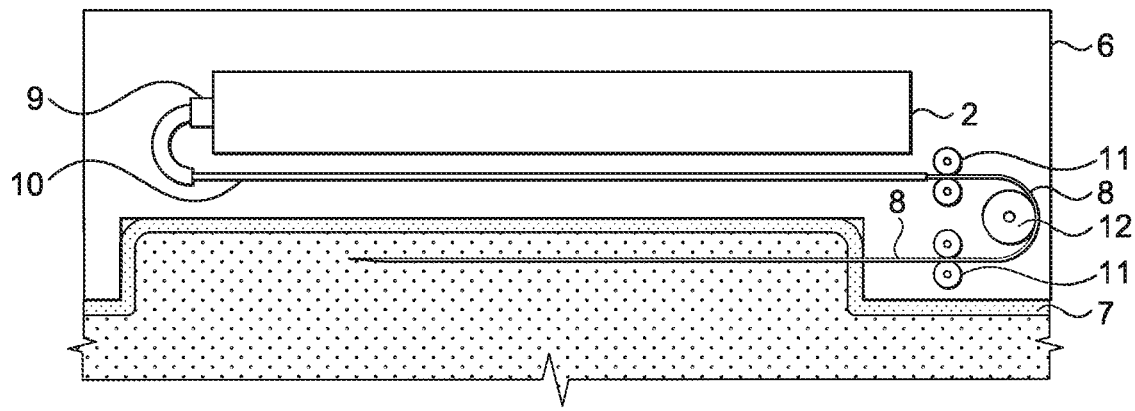
FIG. 4B is a side cross section of a device with a flexible needle after activation.

FIG. 4B is a schematic view of the device shown in FIG. 4A in an activated position showing the needle 8 passed through the guide rollers 11 and 12, out of the device body 6 and into the longitudinal fold of the skin 7.

Figure 5A:
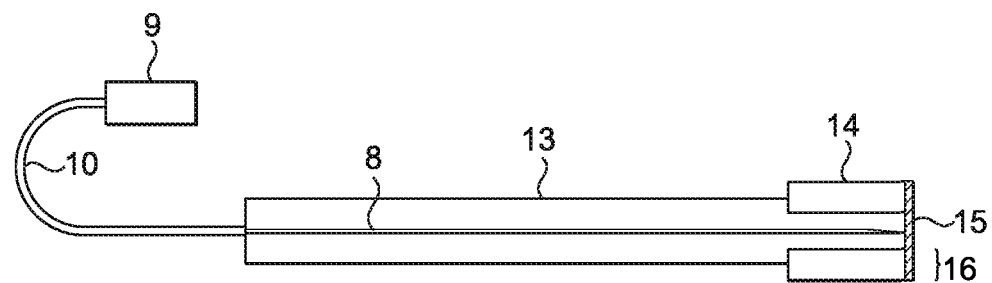
FIG. 5A is a schematic arrangement of a needle with a protecting cover.

FIG. 5A is a schematic view of a needle with a protecting cover or sheath suitable for use in the invention. The connecting hub 9 of the needle is shown connected to the flexi portion of the needle 10, which in turn is directly connected to the rigid portion of the needle 8. The rigid portion 8 includes the needle tip that is intended to penetrate the skin. The needle tip is shrouded in a rigid section 14 of a sheath, with a needle sheath tip section 15 that is penetrable by the needle, encased by rigid walls of the sheath tip region 16, and a flexi-compressible and collapsible sheath 13 section. The flexi section of the needle 10, allows the rigid section to be moved along a distance without requiring the entire needle to be rigid which would require substantially more space to accommodate.

The compressible and collapsible sheath serves two functions. Firstly, to enable the needle to be guided through the guide rollers 11 (not shown here), by allowing the guide rollers 11 to compress against the rigid section of needle 8 itself rather than just compressing the sheath which would lead to just the sheath being pulled across through the guide rollers (since all needle sheaths are generally rigid plastic materials). Secondly, to enable the needle to pass through the penetrable sheath tip 15, and by doing avoiding the need for the user to have to remove the protective sheath around the needle during use. When the needle has been used and retracts back to its rest position the needle tip will return back within the rigid portion of the protective sheath thus preventing any needle stick injuries.

Figure 5B:
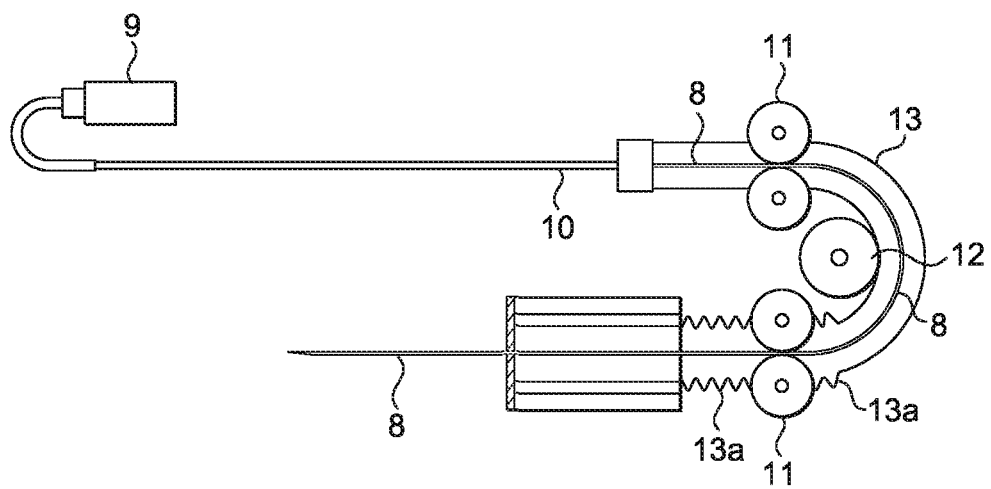
FIG. 5B is a schematic view of the sheathed needle schematic in active position.

FIG. 5B is a schematic illustration of the penetration of the needle tip through the sheath and indicates the guide rollers 11 compressing against the needle and not restricted by the sheath outer wall 13, which is compressed by the guide rollers. Reference 13a indicates the sheath collapsing against the end of the needle sheath tip as the needle moves out of the sheath.

Figure 6:
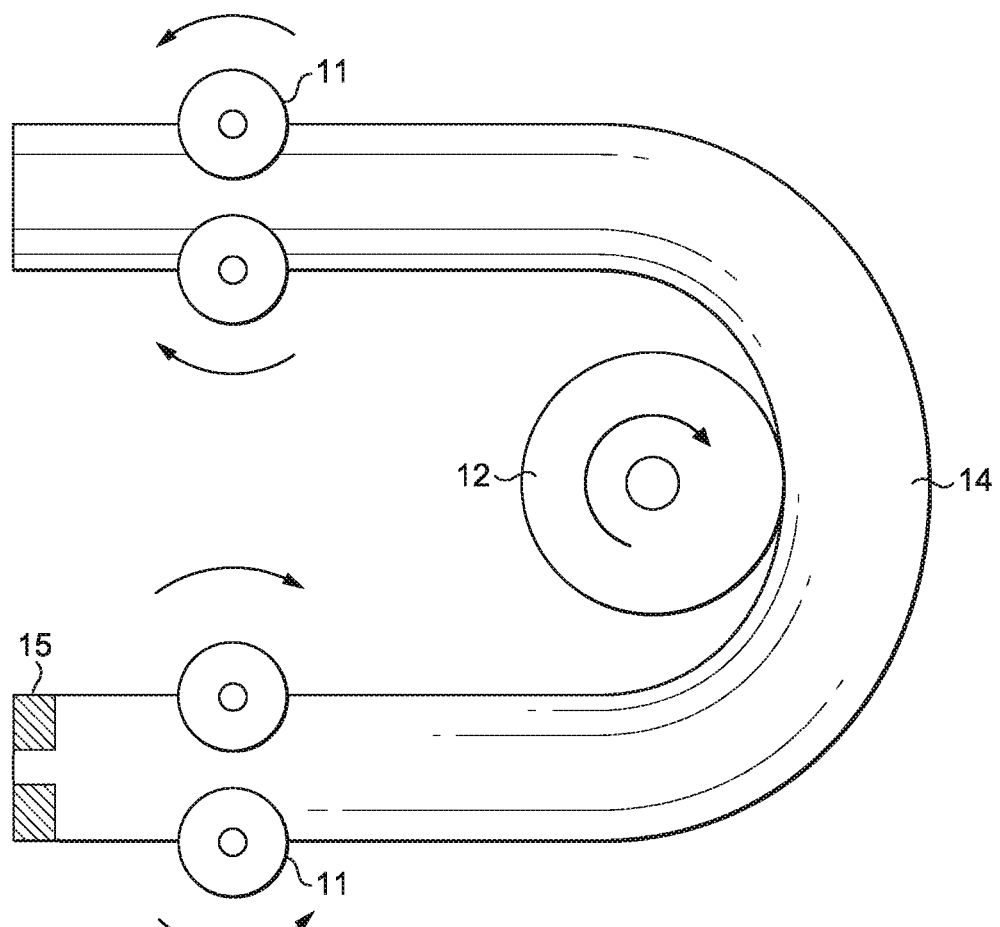
FIG. 6 is a schematic of a guide track for the needle/sheath.

FIG. 6 is a schematic view of the guide track for the needle/sheath. This figure illustrates the guide track within which the needle and associated needle sheath pass through, showing a rigid wall with opening 15, whereby the needle sheath 13 will not be able to pass beyond the rigid wall with opening 15. However, the needle tip will at this point emerge past the sheath rigid tip wall 16, through the opening 15 allowing the collapsible and compressible sheath section to collapse as the needle exits the sheath.

Figure 7A:
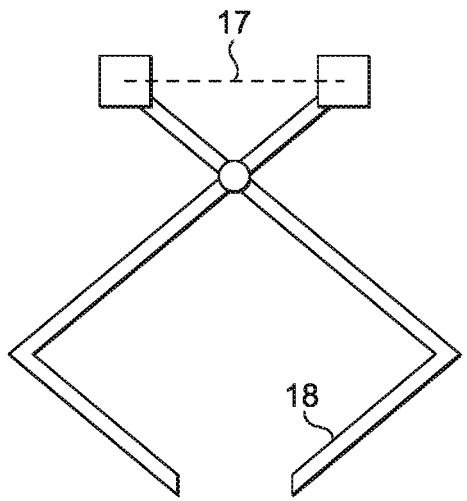
FIG. 7A is a schematic illustration of a mechanism for operating the skin pinch member before activation.
Figure 7B:
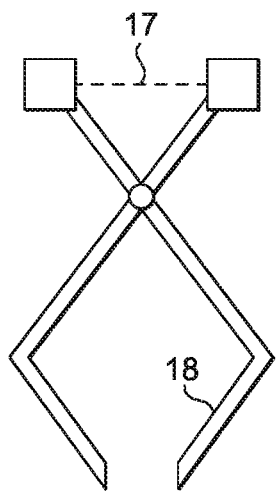
FIG. 7B is a schematic illustration of a mechanism for operating the skin pinch member after activation.

FIGS. 7A and 7B are schematic illustrations of one mechanism for operating the skin pinching members, showing the rest position (A) and active position (B). A compressible section 17 is linked to two arms 18 in a scissor like manner, such that when the compressible section is compressed the tips of the arms come closer together, and in the process, pinch the skin.

Figure 8A:
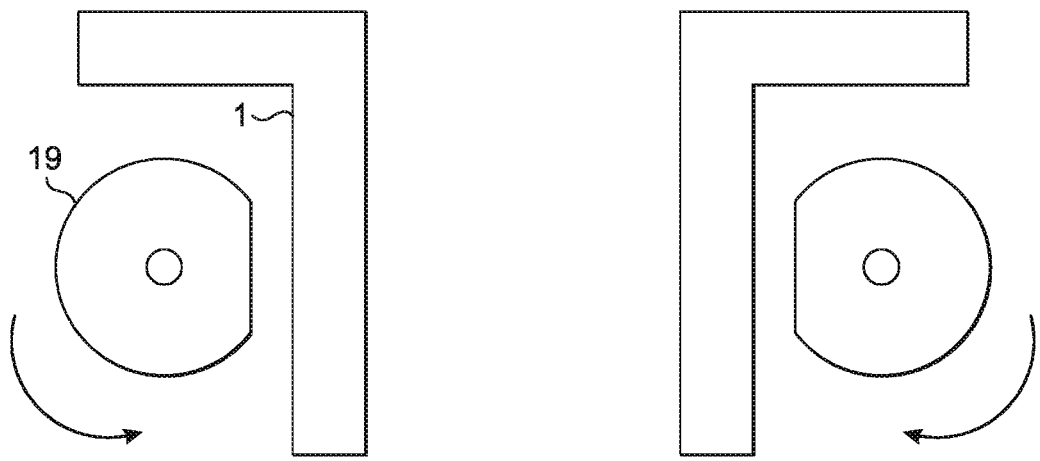
FIG. 8A is a schematic illustration of another mechanism for operating the skin pinch member before activation.
Figure 8B:
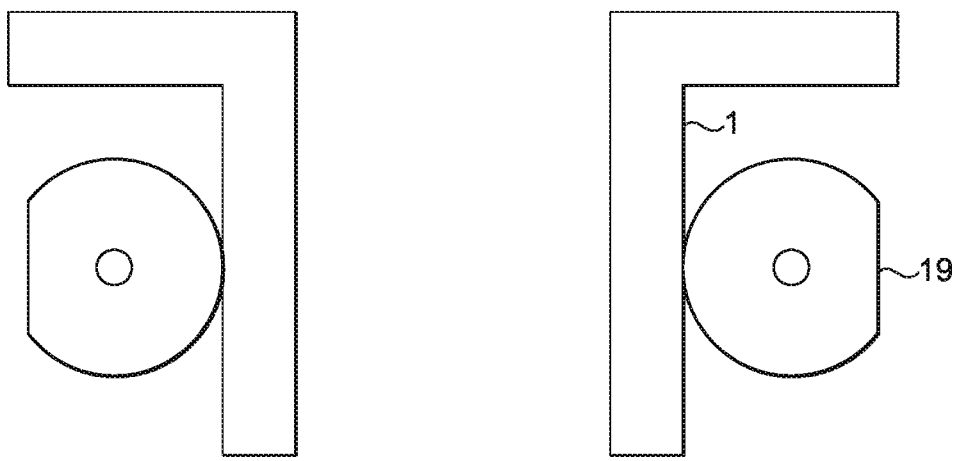
FIG. 8B is a schematic illustration of another mechanism for operating the skin pinch member after activation.

FIGS. 8A and 8B are schematic illustrations of one mechanism for operating the skin pinching members, showing the rest position (A) and active position (B). A cam mechanism 19 is depicted for the activation of the skin pinching members 1. Rotation of the cam mechanism moves the skin pinching members towards each other.

Figure 9A:
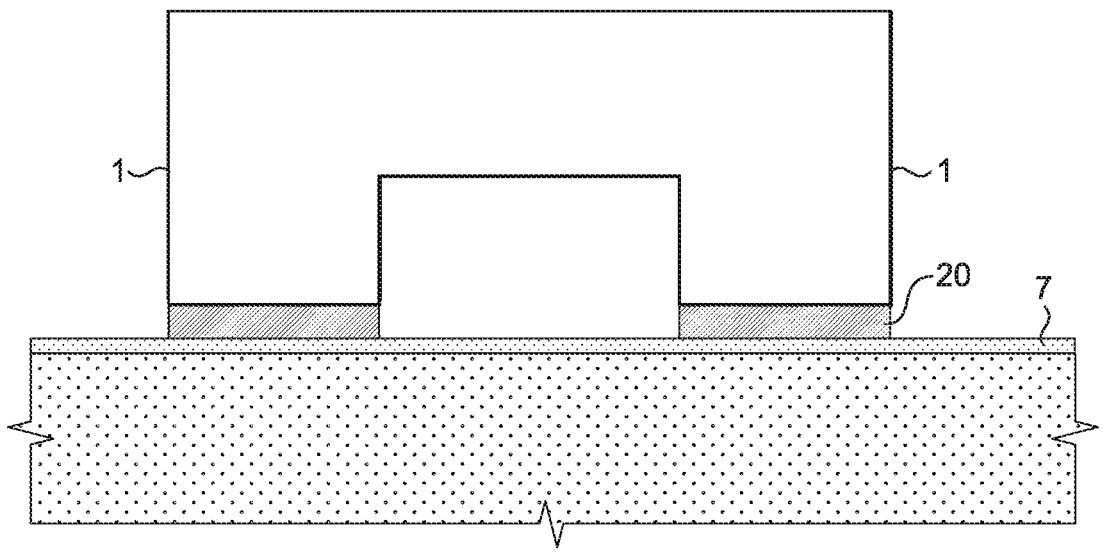
FIG. 9A is a schematic view of a skin pinching member engagement mechanism.
Figure 9B:
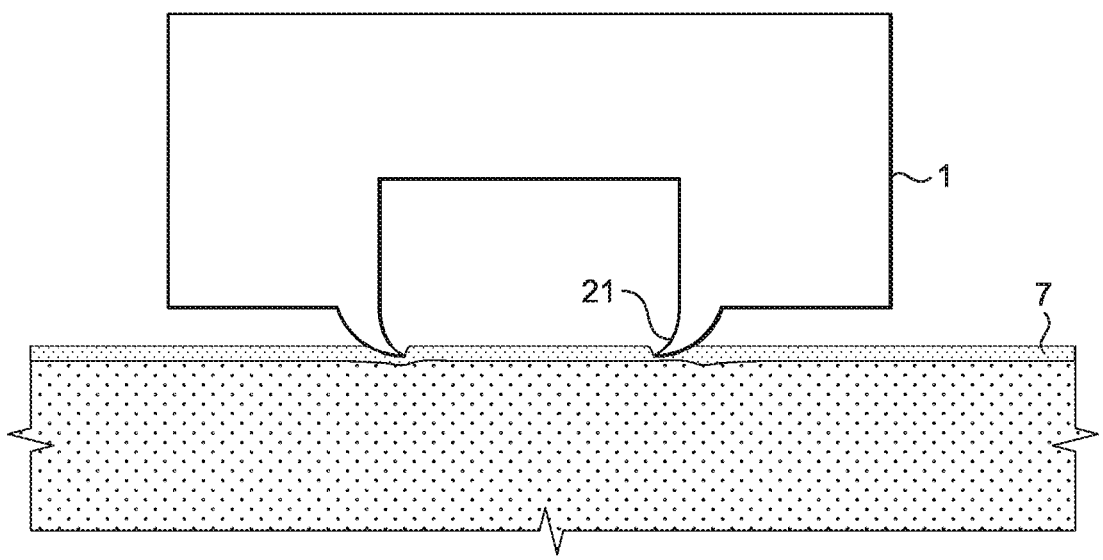
FIG. 9B is a schematic view of another skin pinching member engagement mechanism.

FIGS. 9A and 9B show possible ways for the skin pinching members to engagement the skin of the patient. FIG. 9A shown an adhesive portion 20 that holds the skin pinching members 1 adhered to the skin, whereas FIG. 9B illustrates a mechanical tip region that engages the skin, the purpose being to restrain the skin firmly whilst the skin pinch member is activated. In the case of the adhesive any pressure sensitive adhesive such as silicone, acrylic or synthetic rubber type adhesives may be used.

Figure 10:
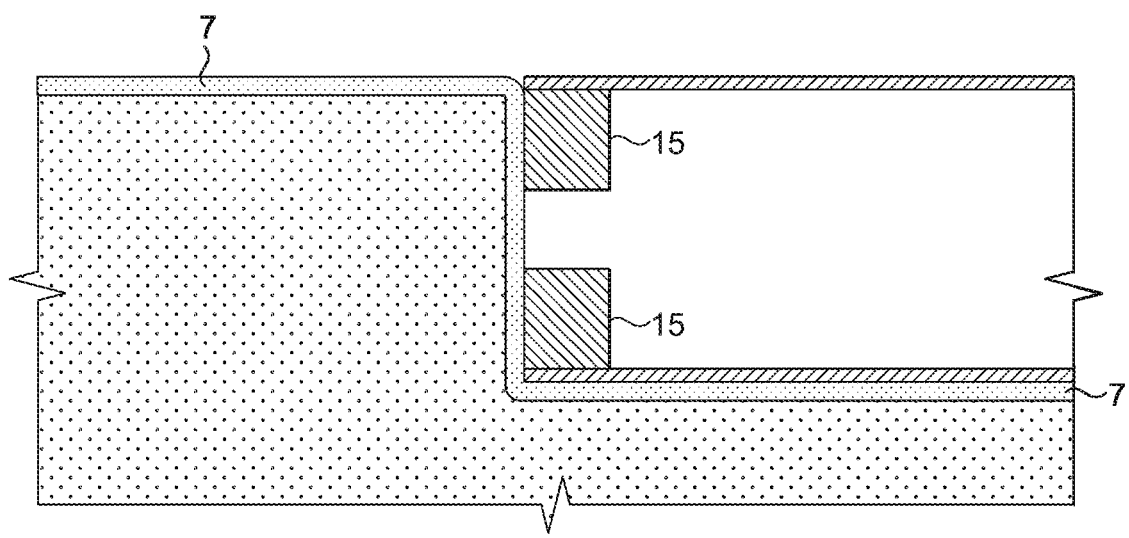
FIG. 10 is a cross sectional view of skin against a needle exit port.

FIG. 10 is a cross section of the patient's skin against a needle exit port. The cross-section schematic shows a fold of skin 7 fitting within a chamber of the device between the needle pinch member, in the active position, where the skin 7 is raised and fits to conform to the shape and volume of the chamber. The skin 7 also rests against the terminal portion of the rigid needle sheath housing 15, through which the needle will protrude and penetrate in to the skin.

The skin is firmly held in place to ensure the needle can pierce the skin without the skin giving way and moving out of position which may lead to the needle penetration the skin at an incorrect depth. The pinch mechanism will therefore ensure the skin is pressed against the sheath tip 15, and this may be achieved by ensuring the skin pinch member overlaps with the region where the needle tip and associated rigid sheath is positioned. This ensure that there is extra skin pinched to fill the chamber between the skin pinch member, since if the skin pinch member is short of the tip of the needle, and not overlapping, then the skin in that latter region may not be adequately under tension and may give way when the needle starts to penetrate it.

Figure 11:
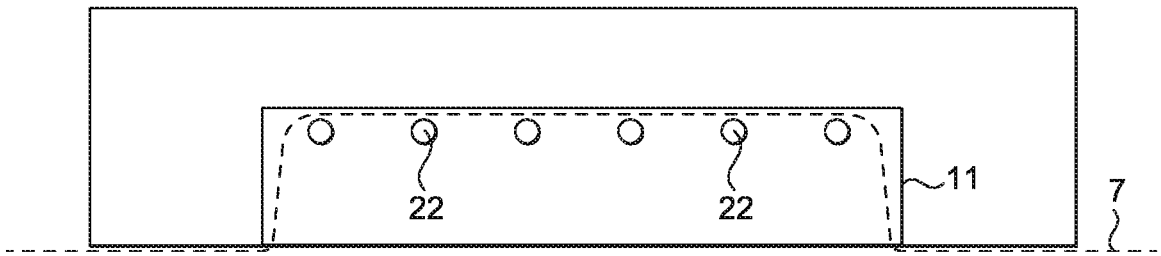
FIG. 11 is a cross sectional view of the device showing optical sensors.

FIG. 11 is a cross sectional view of a device showing optical sensors. The skin 7 is shown in the pinched position by the skin pinching members 1. The device also comprises optical sensors 22 interspersed across the length of the pinch members to detect and ensure that the skin is evenly pinched. A standard light emitting diode available widely, and suitable photo diode to detect the light is positioned and the electronic feedback will prevent the drug being injected until all the diodes are obscured by the skin.

Figure 12A:
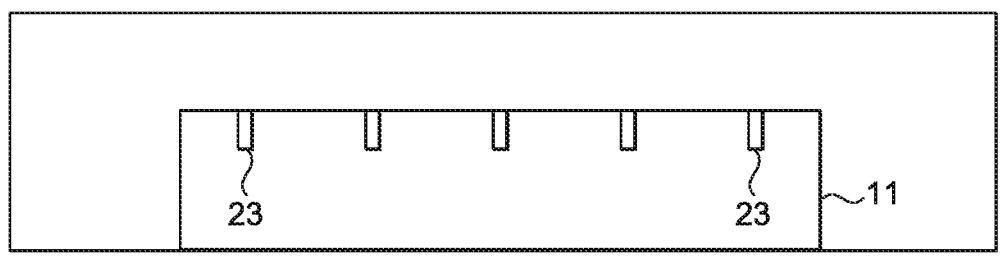
FIG. 12A is a cross sectional view of the device showing mechanical sensors.
Figure 12B:
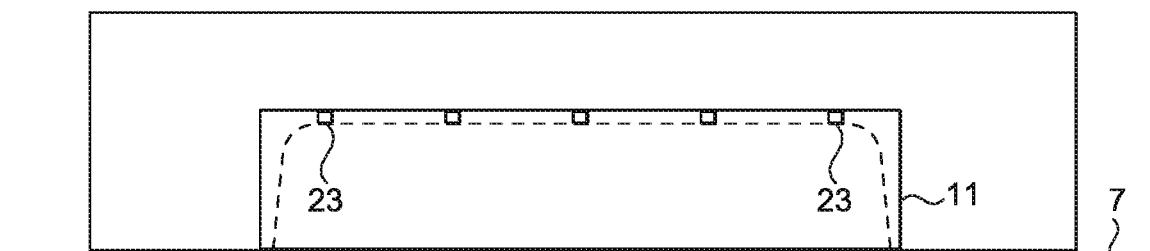
FIG. 12B is a cross sectional view of the device showing activated mechanical sensors.

FIGS. 12A and 12B are cross sectional views of a device showing optical mechanical detection of skin pinch uniformity. Mechanical switches 23 are shown in the roof of the chamber within which the skin gathers as it is pinched, shown in the rest position (A) and activated position (B). Contact of the fold of skin against the mechanical switches indicates the correct pinching of skin.

Figure 13A:
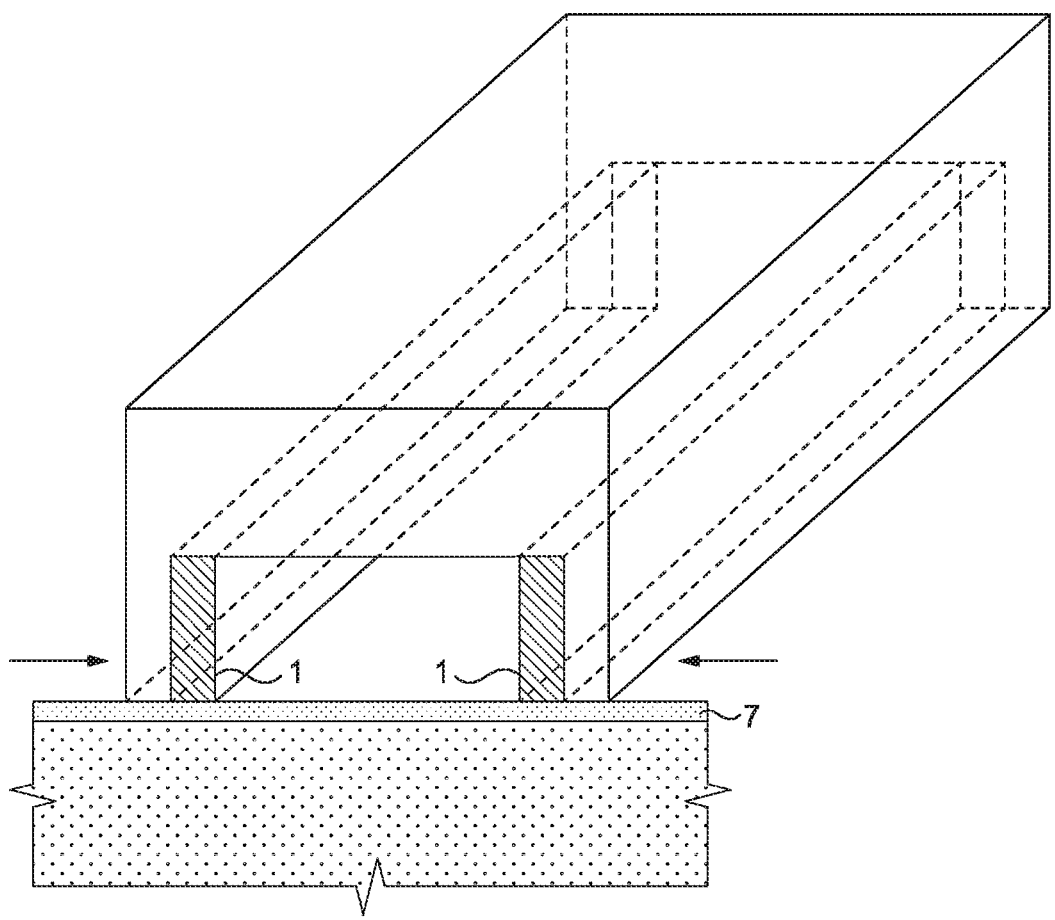
FIG. 13 is a schematic perspective view of the device.
Figure 13B:
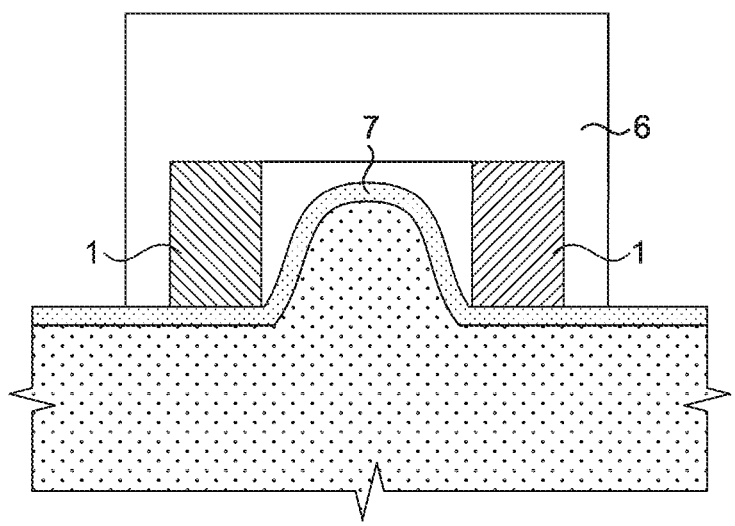

FIG. 13 shows perspective views of a device of the invention, indicating the longitudinal nature of the device. The device body 6 is shown being placed on the skin 7 of the patient, with the skin pinching members 1 spaces wide apart before activation.

Upon activation, the skin pinching members 1 are moved towards each other, creating a fold of skin tissue 7 therebetween. A longitudinal fold of skin 7 is thus formed along the length of the skin pinching members 1.

1 longitudinal skin pinch member
2 Drug reservoir
3 drug reservoir distal/exit end with luer slip or luer lock connection port
4 Electronic control box
5 Needle hub mechanism accommodating the flexible needle
6 Outer housing of injector device
7 skin
8 bendable rigid needle
9 connection port on flexi-rigid needle
10 flexi portion of needle
11 compressing guide rollers for needle
12 single large guide roller for needle
13 Needle sheath/protecting cover flexi-rigid/compressible
14 rigid portion with narrow needle locating orifice within flexi-rigid/compressible needle sheath
15 terminal portion of needle sheath penetrable by needle
16 rigid guide wall of terminal portion of needle sheath
17 contracting mechanism for longitudinal skin pinching member
18 skin pinching member pinching arms
19 Cam mechanism for operating skin pinching member 1
20 Adhesive for gripping skin
21 mechanical protrusion for gripping skin
22 optical detection mechanism for skin pinching consistency
23 mechanical switch detection mechanism for skin pinching consistency

The invention claimed is:

1. A method of sensing the pinching of a longitudinal fold of skin comprising;
   placing a needle delivery device in contact with the skin of a patient, the needle delivery device comprising:
      a device body;
      one or more skin pinching members attached to the device body, the one or more skin pinching members being moveable to pinch the longitudinal fold of skin of the patient;
      a drive mechanism configured, in use, to drive a needle along a needle path, into the longitudinal fold of skin pinched between the one or more skin pinching members, and subsequently withdraw the needle, the needle path extending within the device body, passing out of the device body and extending substantially parallel to the longitudinal fold of skin; and
      at least one sensor mechanism including a plurality of sensors interspersed along a length of an inner surface of at least one of the one or more skin pinching members and being configured to detect pinching along a length of the longitudinal fold of skin;
   moving at least one of the one or more skin pinching members to pinch the longitudinal fold of skin; and
   sensing the pinching of the longitudinal fold of skin and confirming the uniformity of the longitudinal fold of skin along its length with the at least one sensor mechanism.

2. The method according to claim 1, wherein the needle delivery device further comprises a pharmaceutical composition delivery mechanism configured, in use, to deliver a pharmaceutical composition through the needle.

3. The method according to claim 1, which comprises a pharmaceutical composition reservoir in fluid communication with the pharmaceutical composition delivery mechanism.

4. The method according to claim 1, wherein the needle path changes direction as the needle path leaves the device body.

5. The method according to claim 1, wherein the needle delivery device further comprises at least one needle.

6. The method according to claim 5, wherein at least a portion of the at least one needle is flexible.

7. The method according to claim 6, wherein the at least one needle is configured to revert to an elongated straight shape after passing through an arcing pathway.

8. The method according to claim 5, wherein the needle delivery device further includes a guide member configured to guide the at least one needle along the needle path.

9. The method according to claim 8, wherein the guide member is, or includes, a roller.

10. The method according to claim 5, wherein when positioned within the device body the at least one needle is covered by a protective sheath.

11. The method according to claim 10, wherein the protective sheath has a rigid section and a flexible section, wherein the rigid section surrounds a tip of the at least one needle and comprises an opening to allow the at least one needle to exit the rigid section on actuation of the drive mechanism.

12. The method according to claim 11, wherein the protective sheath comprises a sealing membrane covering the opening, wherein the sealing membrane is penetrable by the at least one needle.

13. The method according to claim 5, wherein the at least one needle has a length of greater than about 12 mm.

14. The method according to claim 1, wherein the one or more skin pinching members are configured to automatically adjust based on a volume of a pharmaceutical composition to be injected into the skin; or wherein the plurality of sensors include pressure sensors, and wherein the one or more skin pinching members are configured to automatically adjust based on the pressure of the pinched skin measured by the pressure sensors.

15. The method according to claim 1, wherein the plurality of sensors comprise at least one light source and at least one light sensor to detect the presence of pinched skin therebetween.

16. The method according to claim 1, wherein the plurality of sensors comprise at least one mechanical switch to detect contact with pinched skin.

17. The method according to claim 1, wherein the plurality of sensors comprise an electrical sensor to detect contact with pinched skin.

18. The method according to claim 1, wherein the plurality of sensors include a pressure sensor.

* * * * *